US005707804A

United States Patent [19]
Mathies et al.

[11] Patent Number: 5,707,804
[45] Date of Patent: *Jan. 13, 1998

[54] PRIMERS LABELED WITH ENERGY TRANSFER COUPLED DYES FOR DNA SEQUENCING

[75] Inventors: Richard Mathies, El Cerrito; Alexander Glazer, Orinda; Jingyue Ju, Berkeley, all of Calif.

[73] Assignee: The Regents of the University of California, Oakland, Calif.

[*] Notice: The term of this patent shall not extend beyond the expiration date of Pat. No. 5,654,419.

[21] Appl. No.: 410,808

[22] Filed: Mar. 27, 1995

Related U.S. Application Data

[63] Continuation-in-part of Ser. No. 189,924, Feb. 1, 1994.
[51] Int. Cl.$^6$ .............................. C12Q 1/68; C07H 21/04
[52] U.S. Cl. ................................... 435/6; 536/24.3
[58] Field of Search .................. 435/6; 536/23.1, 536/24.3

[56] References Cited

U.S. PATENT DOCUMENTS

| | | | |
|---|---|---|---|
| 4,855,225 | 8/1989 | Fung et al. | 435/6 |
| 4,868,103 | 9/1989 | Stavrianopoulos et al. | 435/5 |
| 4,996,143 | 2/1991 | Heller et al. | 435/6 |
| 5,188,934 | 2/1993 | Menchen et al. | 435/6 |
| 5,326,692 | 7/1994 | Brinkley et al. | 435/6 |
| 5,342,789 | 8/1994 | Chick et al. | 436/501 |

FOREIGN PATENT DOCUMENTS

| | | | |
|---|---|---|---|
| 86116652.3 | 12/1986 | European Pat. Off. | C12Q 1/68 |
| WO9214845 | 9/1992 | WIPO | C12Q 1/68 |
| WO9309128 | 5/1993 | WIPO | C07H 21/04 |
| WO9417397 | 8/1994 | WIPO | G01N 27/26 |

OTHER PUBLICATIONS

Parkhurst and Parkhurst (Jan. 1995) *Biochemistry* 34:293–300.
Parkhurst and Parkhurst, Jan. 1995, *Biochemistry* 34:285–292.
McKeown et al. (1994) *Biotechniques* 17:901–907.
Fregeau and Fourney (1993) *BioTechniques* 15:100–119.
Benson et al. (1993) *Nucelic Acids Research* 21:5720–5726.
Hiyoshi and Hosoi (Sep. 1994) *Anal. Biochem.* 221:306–11.
Frey (1994) *Cytometry* 17:310–318.
Sixou et al. (Feb. 25, 1994) *Nucleic Acids Research* 22:662–8.

Wei et al. (1994) *Anal. Biochem.* 66:1500–6.
Ju et al., Fluorescence Energy Transfer Dye–Labeled Primers for DNA Sequencing and Analysis, (1995) *Proc. Natl. Acad. Sci. USA*, 92:4347:4351.
Smith et al., Fluorescence Detection in Automated DNA Sequence Analysis, (1986) *Nature*, 321:674–679.
Prober et al., A System For Rapid DNA Sequencing With Fluorescent Chain–Terminating Dideoxynucleotides, (1987) *Science*, 238:336–341.
Ansorge et al., Automated DNA Sequencing: Ultrasensitive Detection of Fluorescent Bands During Electrophoresis, (1987) *Nucleic Acids Research*, vol. 15 No. 11:4593–4603.
Huang et al., DNA Sequencing Using Capillary Array Electrophoresis, (1992) *Anal. Chem.*, 64:2149–2154.
Glazer et al., Fluorescent Tandem Phycobiliprotein Conjugates, (1983) *Biophys. J. Biophysical Society*, 43:383–386.
Cardullo et al., Detection Of Nucleic Acid Hybridization By Nonradiative Fluorescence Resonance Energy Transfer, (1988) *Proc. Natl. Acad.*, 85:8790–8794.
Clegg et al., Observing The Helical Geometry Of Double–Stranded DNA In Solution By Fluorescence Resonance Energy Transfer, (1993) *Proc. Natl. Acad. Sci., USA*, 90:2994–2998.
Mergny et al., Fluorescence Energy Transfer As A Probe For Nucleic Acid Structures And Sequences, (1994) *Nucleic Acids Research*, vol. 22, No. 6:920–928.
Selvin et al., Luminescence Energy Transfer Using A Terbium Chelate: Improvements On Fluorescence Energy Transfer, (1994) *Proc. Natl. Acad. Sci, USA*, 91:10024–10028.
L. Stryer, Fluorescence Energy Transfer As A Spectroscopic Ruler[1], (1978) *Ann. Rev. Biochem.*, 47:819–46.
Butler et al., Rapid Analysis Of The Short Tandem Repeat HUMTH01 By Capillary Electrophoresis, (1994) *BioTechniques*, vol. 17, No. 6:1062–1070.

*Primary Examiner*—W. Gary Jones
*Assistant Examiner*—Amy Atzel
*Attorney, Agent, or Firm*—Townsend and Townsend and Crew LLP

[57] ABSTRACT

Compositions are provided for making oligonucleotides carrying pairs of donor and acceptor dye molecules, designed for efficient excitation of the donor at a single wavelength and emission from the acceptor in each of the pairs at different wavelengths. The different molecules having different donor-acceptor pairs can be modified to have substantially the same mobility under separation conditions, by varying the distance between the donor and acceptor in a given pair, and to have enhanced emission intensities from the acceptor. Particularly, the fluorescent compositions find use as labels in sequencing nucleic acids.

13 Claims, 12 Drawing Sheets

F-1-(F,J,T,R)   FAM-5'-GT*TTTCCCAGTCACGAC-3'
  |
  (FAM, JOE, TAMRA, ROX)

F-2-(F,J,T,R)   FAM-5'-GTT*TTCCCAGTCACGACG-3'
  |
  (FAM, JOE, TAMRA, ROX)

F-3-(F,J,T,R)   FAM-5'-GTTT*TCCCAGTCACGACG-3'
  |
  (FAM, JOE, TAMRA, ROX)

F-4-(F,J,T,R)   FAM-5'-GTTTT*CCCAGTCACGAC-3'
  |
  (FAM, JOE, TAMRA, ROX)

F-10-(F,J,T,R)   FAM-5'-GTTTTCCCAGT*CACGAC-3'
  |
  (FAM, JOE, TAMRA, ROX)

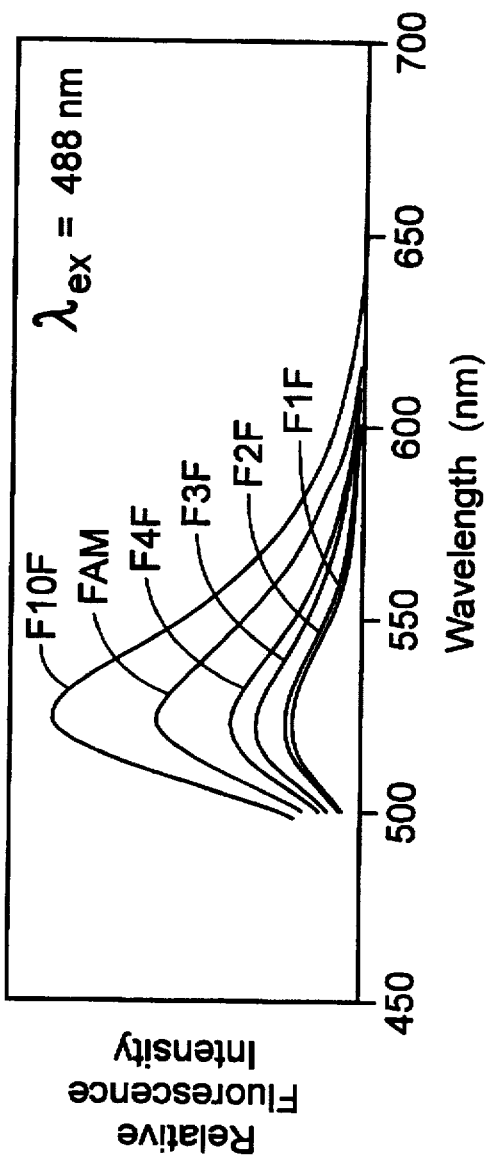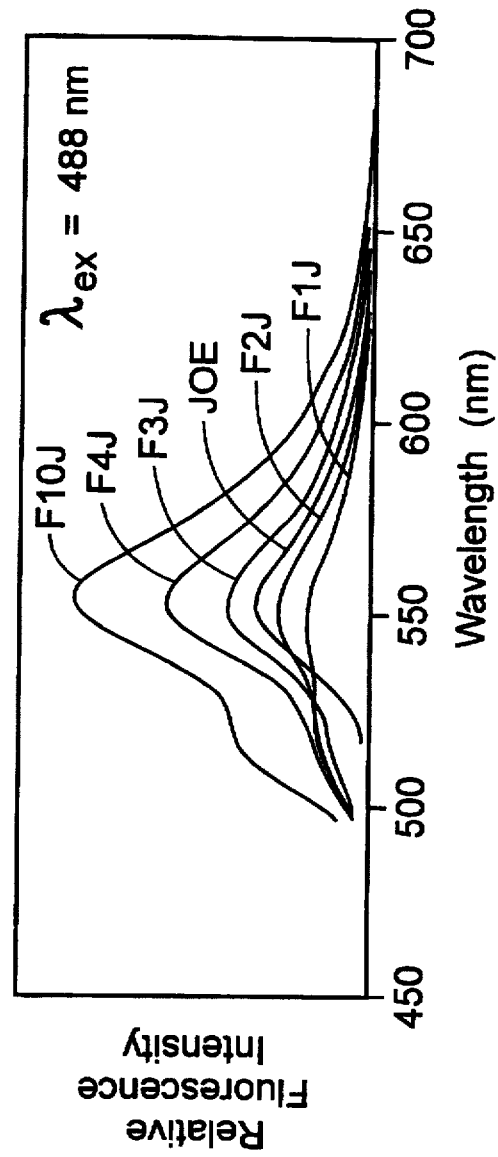
Fig. 4a
Fig. 4b

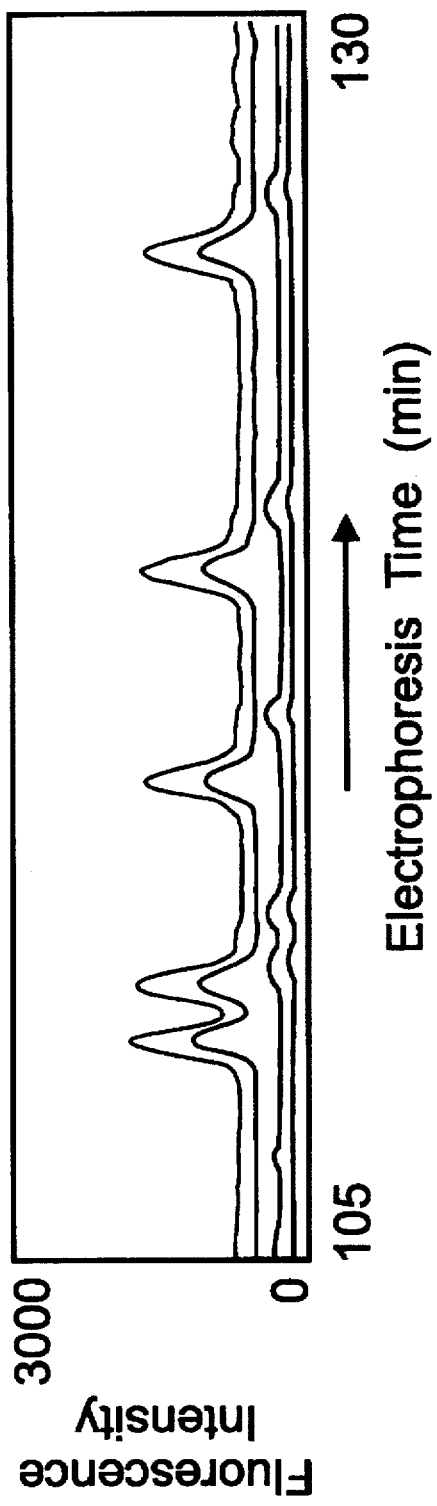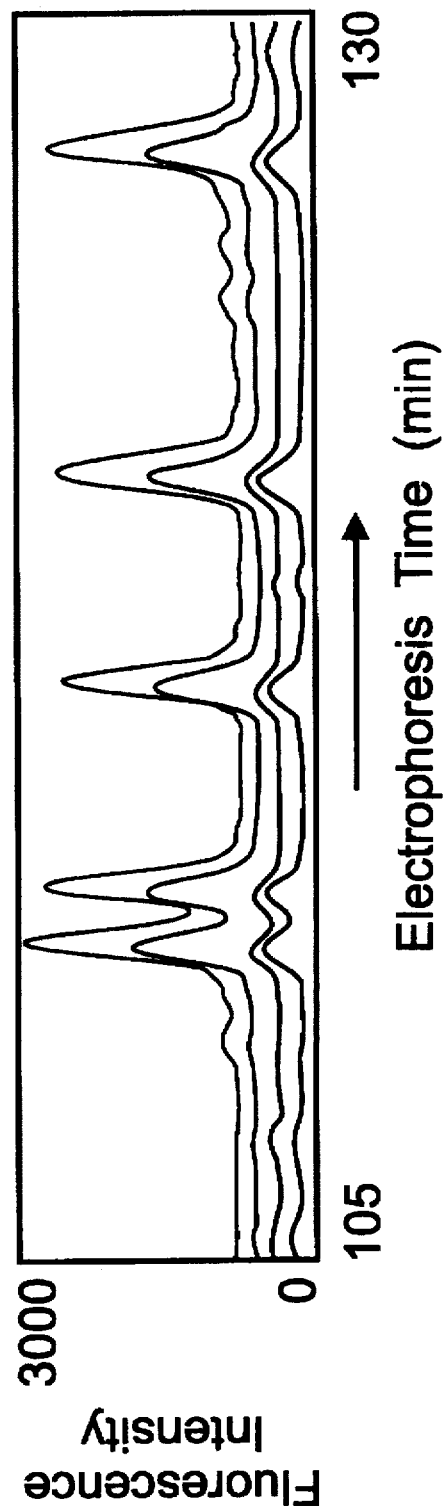

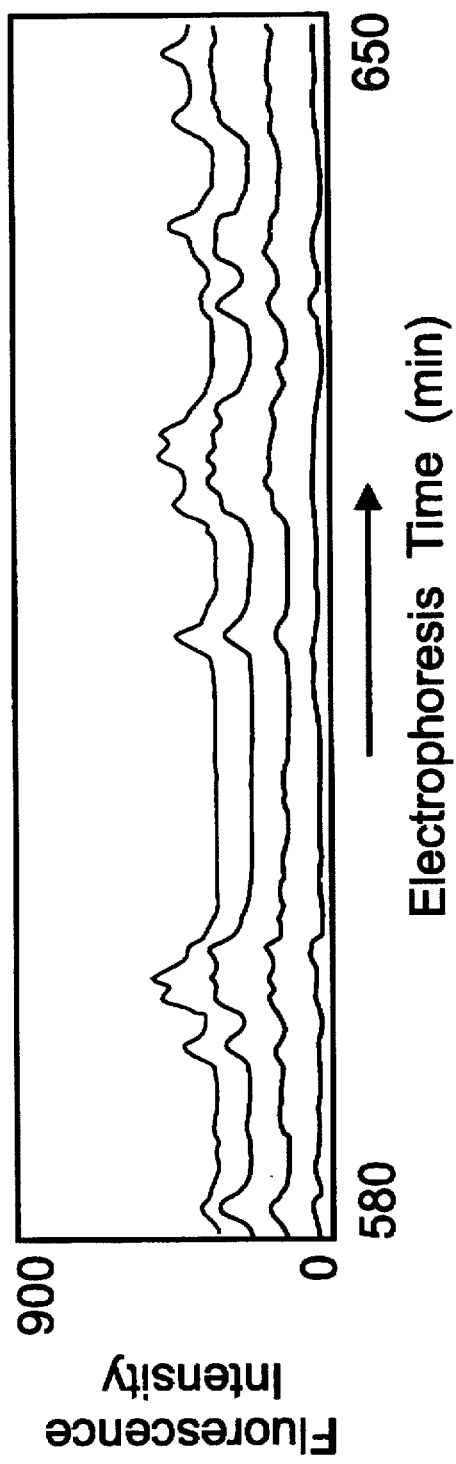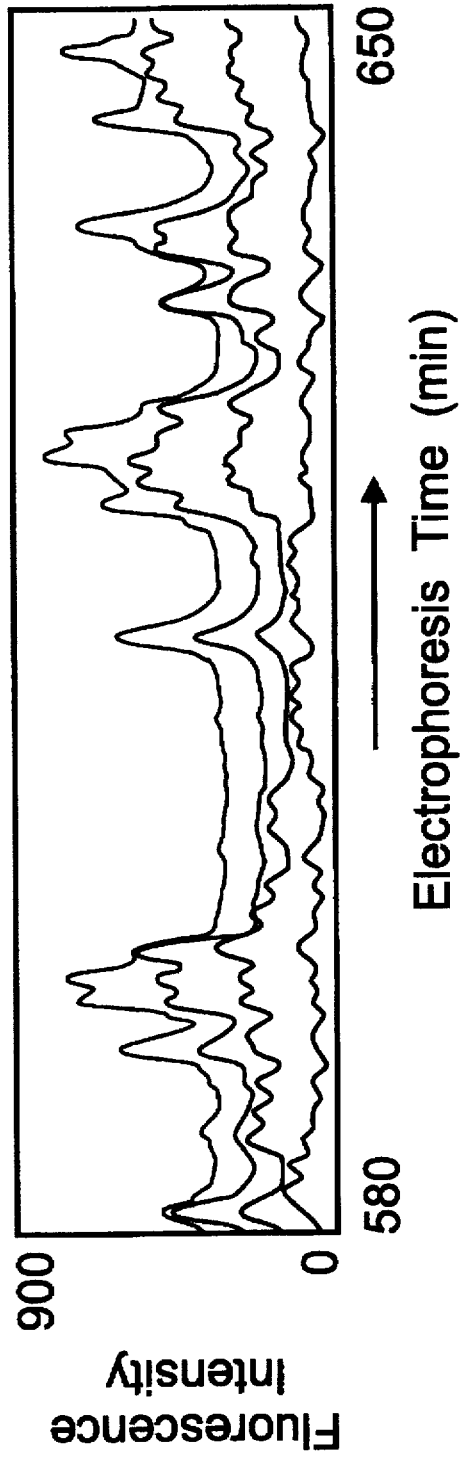

PRIMERS LABELED WITH ENERGY TRANSFER COUPLED DYES FOR DNA SEQUENCING

CROSS-REFERENCE TO RELATED APPLICATION

This application is a continuation-in-part of application Ser. No. 08/189,924, filed Feb. 1, 1994.

TECHNICAL FIELD

The field of this invention is fluorescent tags and their use for DNA sequencing.

BACKGROUND

There is an increasing demand to be able to identify and quantify components of mixtures. The greater the complexity of the mixture, the greater the interest in being able to simultaneously detect a plurality of the components present. As illustrative of this situation is DNA sequencing, where it is desirable to efficiently excite from one to four fluorescently tagged components with a laser source at a single wavelength, while providing for fluorescent signal emission at a plurality of distinctive wavelengths. In this situation, the different labels should not adversely affect the electrophoretic mobility of the sequences to which they are attached.

Currently, there are four methods used for automated DNA sequencing: (1) the DNA fragments are labeled with one fluorophore and then the fragments run in adjacent sequencing lanes (Ansorge et al., *Nucleic Acids Res.* 15, 4593–4602 (1987); (2) the DNA fragments are labeled with four different fluorophores and all the fragments are electrophoretically separated and detected in a single lane (Smith et al., *Nature* 321, 674–679 (1986); (3) each of the dideoxynucleosides in the termination reaction is labeled with a different fluorophore and the four sets of fragments are run in the same lane (Prober et al., *Science* 238, 336–341 (1987); or (4) the sets of DNA fragments are labeled with two different fluorophores and the DNA sequences coded with the dye ratios (Huang et al., *Anal. Chem.* 64, 2149–2154 (1992).

All of these techniques have significant deficiencies. Method 1 has the potential problems of lane-to-lane variations in mobility, as well as a low throughput. Methods 2, 3 and 4 require that the four dyes be well excited by one laser source and that they have distinctly different emission spectra. In practice, it is very difficult to find two or more dyes that can be efficiently excited with a single laser and that emit well separated fluorescent signals.

As one selects dyes with distinctive red-shifted emission spectra, their absorption maxima will also move to the red and all the dyes can no longer be efficiently excited by the same laser source. Also, as more different dyes are selected, it becomes more difficult to select all the dyes such that they cause the same mobility shift of the labeled molecules.

It is therefore of substantial interest that improved methods be provided which allow for multiplexing of samples, so that a plurality of components can be determined in the same system and in a single run. It is also desirable for each label to have strong absorption at a common wavelength, to have a high quantum yield for fluorescence, to have a large Stokes shift of the emission, that the various emissions be distinctive, and that the labels introduce the same mobility shift. It is difficult to accomplish these conflicting goals by simply labeling the molecules with a single dye.

SUMMARY OF THE INVENTION

The subject invention provides compositions and methods for analyzing a mixture using a plurality of fluorescent labels. To generate the labels, pairs or families of fluorophores are bound to a backbone, particularly a nucleic acid backbone, where one member of each family is excited at approximately a common wavelength. By exploiting the phenomenon of energy transfer, the other members of each of the families emit at detectably different wavelengths. The range of distances between donor and acceptor chromophores is chosen to ensure efficient energy transfer. Furthermore, labels used conjointly are selected to have approximately the same mobility in a separation system. This is achieved by changing the mobility of the labeled entity by varying the distance between the two or more members of the family of fluorophores and choosing labels with the same mobility. The subject invention finds particular application in DNA sequencing, where the fluorophores may be attached to universal or other primers and different fluorophore combinations used for the different dideoxynucleosides. Kits of combinations of labels are also provided.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 2A shows F10F vs. FAM, FIG. 2B shows F10J vs. JOE, FIG. 2C shows F3T vs. TAMRA and FIG. 2D shows F3R vs. ROX. The emission spectra for each primer pair were determined using solution having the same molar concentration.

FIG. 4A, 4B, 4C, and 4D show that the fluorescence emission intensity of the ET primers is increased as the distance between the donor and acceptor increases. The emission spectra for each primer series were determined at the same molar concentration in 1×TBE.

FIGS. 8A, 8B, 8C, 8D and 8E show the comparison of signal strengths and mobility shifts of the single dye-labeled primers and ET primers. A total of eight sequencing reactions with ddTTP/dNTPs were run using 1 µg of M13mp18 DNA template and 0.4 pmol of primer and then loaded in 8 adjacent lanes of the ABI 373A sequencing gel. FIG. 8A shows the raw traces obtained when single dye-labeled primers were used. Colors correspond to the dye as follows: blue, FAM; green, JOE; black, TAMRA; red, ROX. The region shown corresponds to the sequence approximately 15–35 bases from the 3' end of the primer. FIG. 8B shows raw traces on identical scales obtained using ET primers. Colors correspond to the dye as follows: blue, F10F; green, F10J; black, F3T; red, F3R. FIGS. 8C and 8D display data from 4-color sequencing reactions run with single-dye primers (C) and ET primers (D) on identical scales. For reference, the ET primer data in (D) is also shown in analyzed format in FIG. 8E. The reactions used for panel c included 0.4 pmol of FAM and JOE primer; 0.8 pmol of TAMRA and ROX primer, and the reactions for FIGS. 8D and 8E included 0.4 pmol of each ET primer and a total of 6 µg of M13mp18 template DNA.

DESCRIPTION OF SPECIFIC EMBODIMENTS

Figure 1:
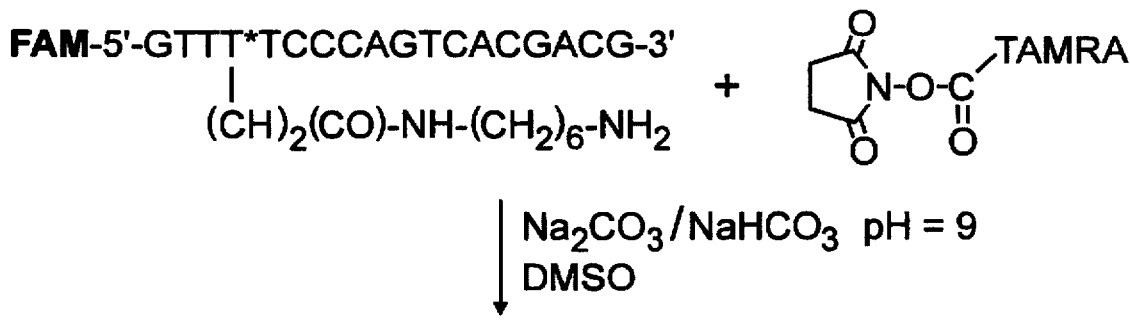
FIG. 1. Structures of the twenty energy transfer (ET) primers and a representative synthetic scheme for the preparation of F3T.
Figure 1:
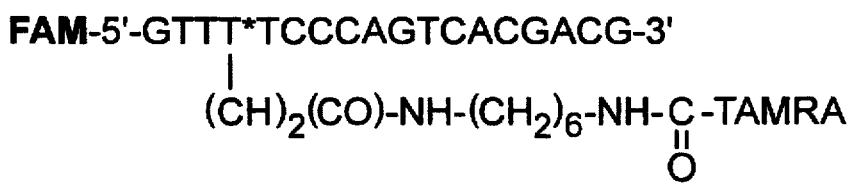
Figure 2A:
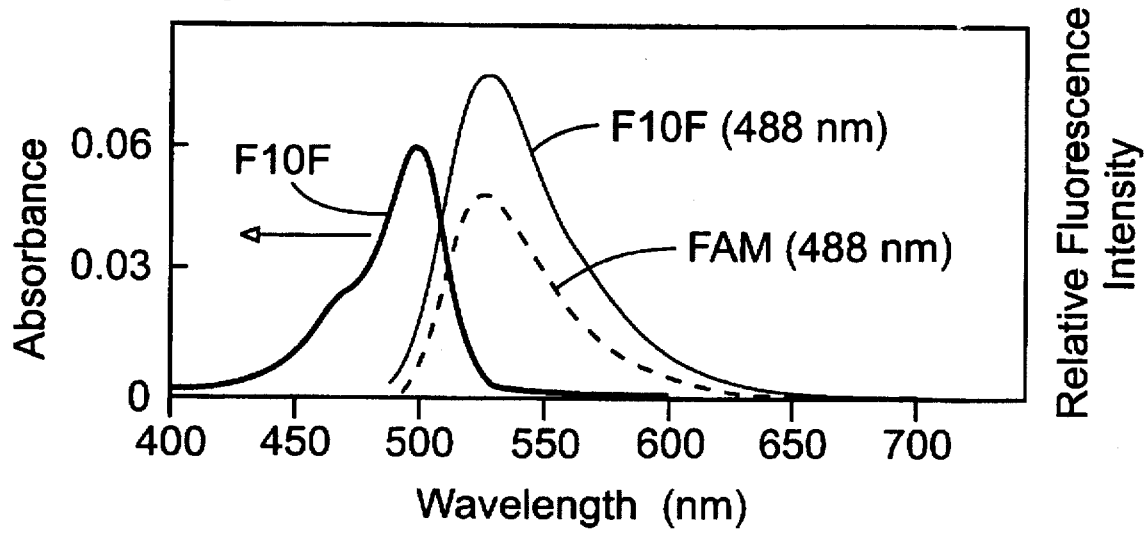
FIG. 2A, 2B, 2C and 2D shows the comparison of the fluorescence emission intensity of the four energy transfer (ET) primers (F10F, F10J, F3T and F3R) with the corresponding single dye-labeled primers at the indicated excitation wavelength (1×TBE, 7M urea). The thick lines indicate the absorption spectra of the ET primers.
Figure 2B:
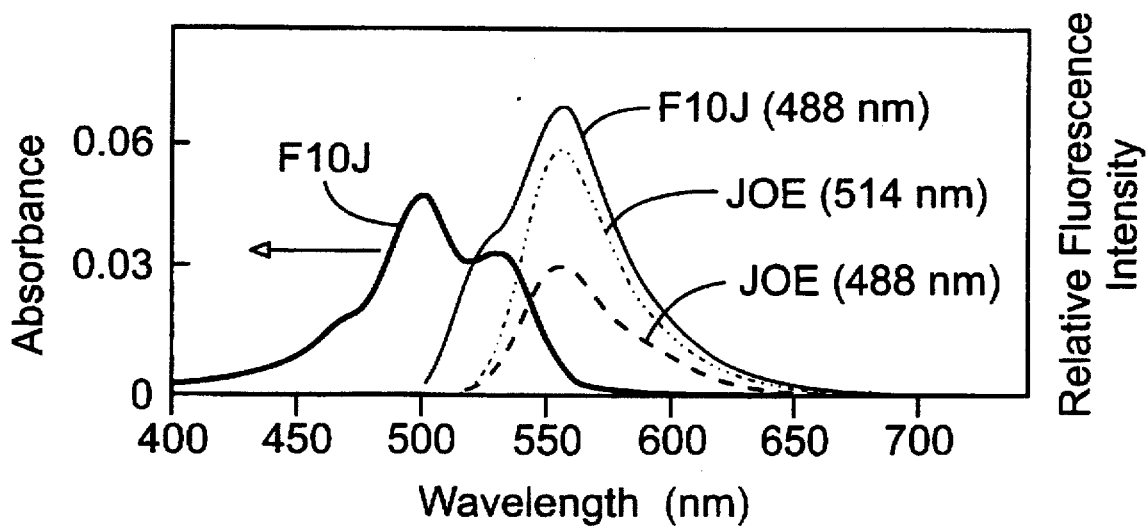
Figure 2C:
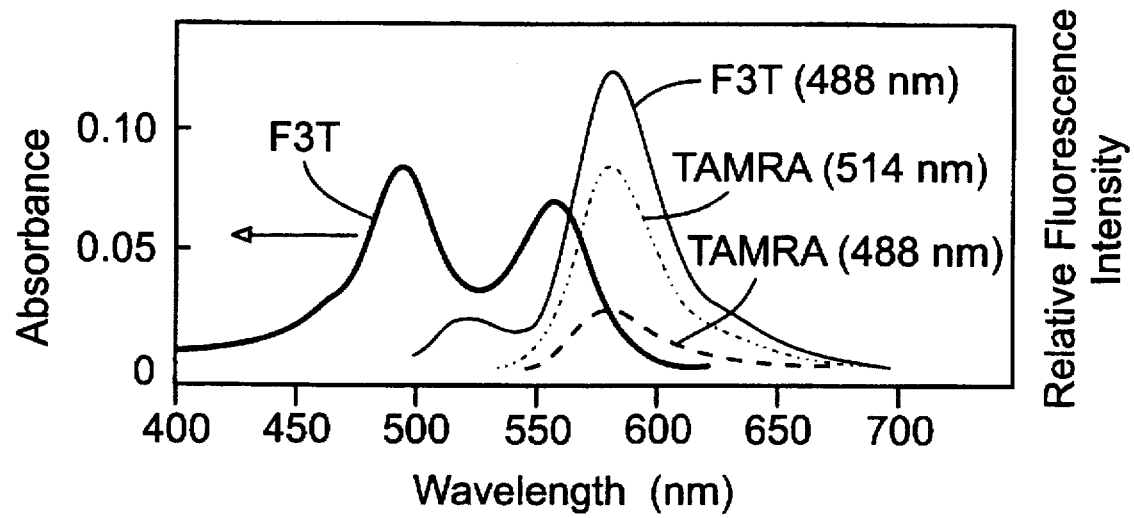
Figure 2D:
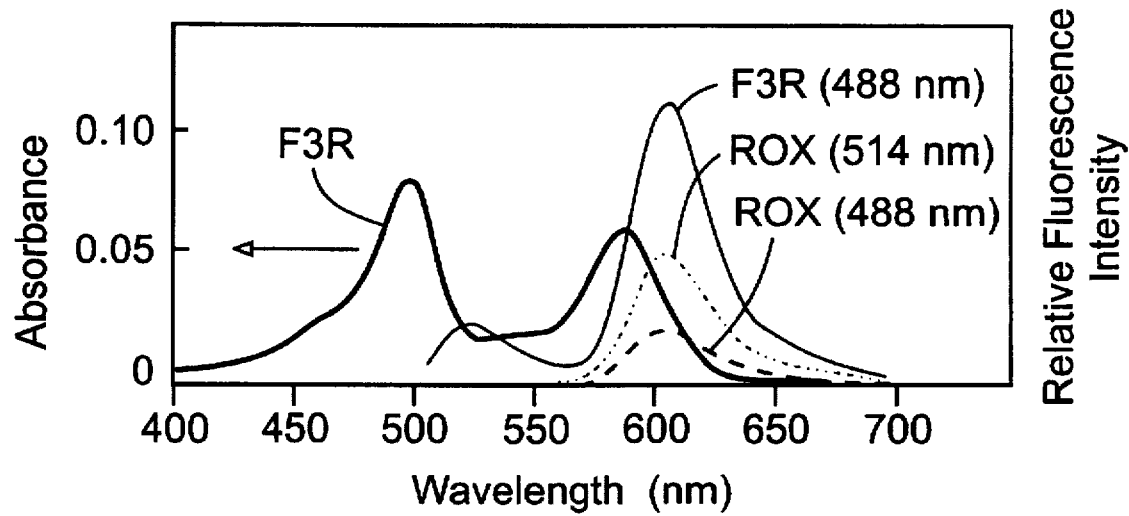

Novel fluorescent labels, combinations of fluorescent labels, and their use in separation systems involving the separation of a plurality of components are provided. Particularly, the fluorescent labels comprise pairs of fluorophores, which with one exception where the fluorophores are the same, involve different fluorophores having overlapping spectra, where the donor emission overlaps the acceptor absorption, so that there is energy transfer from the excited fluorophore to the other member of the pair. It is not essential that the excited fluorophore actually fluoresce, it being sufficient that the excited fluorophore be able to efficiently absorb the excitation energy and efficiently transfer it to the emitting fluorophore.

The donor fluorophores in the different families of fluorophores may be the same or different, but will be able to be excited efficiently by a single light source of narrow bandwidth, particularly a laser source. The door fluorophores will have significant absorption, usually at least about 10%, preferably at least about 20% of the absorption maxima within 20 nm of each other, usually within 10 nm, more usually within 5 nm, of each other. The emitting or accepting fluorophores will be selected to be able to receive the energy from donor fluorophores and emit light, which will be distinctive and detectably different. Therefore, one will be able to distinguish between the components of the mixture to which the different labels have been bound. Usually the labels will emit at emission maxima separated by at least 10 nm, preferably at least 15 nm, and more preferably at least 20 nm.

Usually the donor fluorophores will absorb in the range of about 350–800 nm, more usually in the range of about 350–600 nm or 500–750 nm, while the acceptor fluorophores will emit light in the range of about 450–1000 nm, usually in the range of about 450–800 nm. As will be discussed subsequently, one may have more than a pair of absorbing molecules, so that one may have 3 or more molecules, where energy is transferred from one molecule to the next at higher wavelengths, to greatly increase the difference in wavelength between absorption and observed emission.

The two fluorophores will be joined by a backbone or chain, usually a polymeric chain, where the distance between the two fluorophores may be varied. The physics behind the design of the labels is that the transfer of the optical excitation from the donor to the acceptor depends on $1/R^6$, where R is the distance between the two fluorophores. Thus, the distance must be chosen to provide energy transfer from the donor to the acceptor through the well-known Foerster mechanism. Thus, the distance between the two fluorophores as determined by the number of atoms in the chain separating the two fluorophores can be varied in accordance with the nature of the chain. Various chains or backbones may be employed, such as nucleic acids, both DNA and RNA, modified nucleic acids, e.g. where oxygens may be substituted by sulfur, carbon, or nitrogen, phosphates substituted by sulfate or carboxylate, etc., polypeptides, polysaccharides, various groups which may be added stepwise, such as di-functional groups, e.g. haloamines, or the like. The fluorophores may be substituted as appropriate by appropriate functionalization of the various building blocks, where the fluorophore may be present on the building block during the formation of the label, or may be added subsequently, as appropriate. Various conventional chemistries may be employed to ensure that the appropriate spacing between the two fluorophores is obtained.

The molecular weights of the labels (fluorophores plus the backbone to which they are linked) will generally be at least about 250 Dal and not more than about 10,000 Dal, usually not more than about 8,000 Dal. The molecular weight of the fluorophore will generally be in the range of about 250 to 2,000 Dal, where the molecular weights of the acceptor-donor pairs on different labels to be used together will usually not differ by more than about 20%. The fluorophores may be bound internal to the chain, at the termini, or one at one terminus and another at an internal site. The fluorophores may be selected so as to be from a similar chemical family, such as cyanine dyes, xanthenes or the like. Thus, one could have the donors from the same chemical family, each donor-acceptor pair from the same chemical family or each acceptor from the same family or the combination from a different family.

The subject labels find particular application in various separation techniques, such as electrophoresis, chromatography, or the like, where one wishes to have optimized spectroscopic properties, high sensitivity and comparable influence of the labels on the migratory aptitude of the components being analyzed. Of particular interest is electrophoresis, such as gel, capillary, etc. Among chromatographic techniques are HPLC, affinity chromatography, thin layer chromatography, paper chromatography, and the like.

It is found that the spacing between the two fluorophores will affect the mobility of the label. Therefore, one can use different dye pairs and by varying the distance between the different dye pairs, within a range which still permits good energy transfer, provide for substantially constant mobility for the labels. The mobility is generally not systematically related to the specific spacing, so that one will empirically determine the effect of the spacing on the mobility of a particular label. However, because of the flexibility in the spacing of the fluorophores in the labels, by synthesizing a few different labels with different spacings and different dye pairs, one can now provide for a family of fluorescent labels, which share a common excitation, that have strong and distinctive emission and a substantially common mobility. Usually, the mobility will differ by not more than about 20% of each other, preferably not more than about 10% of each other, and more preferably within about 5% of each other, when used in a particular separation. Generally, this will translate to less than about 1 base difference, preferably not more than about 0.5 base difference. The mobility may usually be determined by carrying out the separation of the labels by themselves or the labels bound to a common molecule which is relevant to the particular separation, e.g. a nucleic acid molecule of the appropriate size, where one is interested in sequencing.

A wide variety of fluorescent dyes may find application. These dyes will fall into various classes, where combinations of dyes may be used within the same class or between different classes. Included among the classes are dyes, such as the xanthene dyes, e.g. fluoresceins and rhodamines, coumarins, e.g. umbelliferone, benzimide dyes, e.g. Hoechst 33258, phenanthridine dyes, e.g. Texas Red, and ethidium dyes, acridine dyes, cyanine dyes, such as thiazole orange, thiazole blue, Cy 5, and Cyfr, carbazole dyes, phenoxazine dyes, porphyrin dyes, quinoline dyes, or the like. Thus, the dyes may absorb in the ultraviolet, visible or infra-red ranges. For the most part, the fluorescent molecules will have a molecular weight of less than about 2 kDal, generally less than about 1.5 kDal.

The energy donor should have strong molar absorbance coefficient at the desired excitation wavelength, desirably greater than about $10^4$, preferably greater than about $10^5$ $cm^{-1}M^{-1}$. The excitation maximum of the donor and the emission maximum of the acceptor (fluorescer) will be separated by at least 15 nm or greater. The spectral overlap integral between the emission spectrum of the donor chromophore and the absorption spectrum of the acceptor chromophore and the distance between the chromophores will be such that the efficiency of energy transfer from donor to acceptor will range from 20% to 100%.

Separation of the donor and acceptor based on number of atoms in the chain will vary depending on the nature of the backbone, whether rigid or flexible, involving ring structures or non-cyclic structures or the like. Generally the number of atoms in the chain (the atoms in the ring structures will be counted as the lowest number of atoms around one side of the ring for inclusion in the chain) will be below about 300, usually below about 200 atoms, preferably below about 150, where the nature of the backbone will influence the efficiency of energy transfer between donor and acceptor. Conveniently, one of the dyes may be on the 5' or 3' terminal nucleoside.

While for the most part, pairs of fluorophores will be used, there can be situations where up to four different, usually not more than three different, fluorophores bound to the same backbone may find use. By using more fluorophores, one may greatly extend the Stokes shift, so that one may excite in the visible wavelength range and have emission in the infra-red wavelength range, usually below about 1000 nm, more usually below about 900 nm. Detecting light in the infra-red wavelength range has many advantages, since it will not be subject to interference from Raman and Rayleigh light resulting from the excitation light. In order to maintain the mobility constant, one may use the same number of fluorophores on the labels, having a multiplicity of the same fluorophore to match the number of fluorophores on labels having different fluorophores for the large Stokes shift.

The subject invention finds particular application with nucleic acid chains, where the nucleic acid chains find use as primers in sequencing, the polymerase chain reaction, particularly for sizing, or other system where primers are employed for nucleic acid extension and one wishes to distinguish between various components of the mixture as related to the particular labels. For example, in sequencing, universal primers may be employed, where a different pair of fluorophores are used for each of the different dideoxynucleosides used for the extension during sequencing reactions.

A large number of nucleosides are available, which are functionalized, and may be used in the synthesis of a polynucleotide. By synthesizing the subject nucleic acid labels, one can define the specific sites at which the fluorophores are present. Commercially available synthesizers may be employed in accordance with conventional ways, so that any sequence can be achieved, with the pair of fluorophores having the appropriate spacing.

As already indicated, the subject labels find particular use in sequencing. For example, universal primers may be prepared, where the primer may be any one of the universal primers, having been modified by bonding of the two fluorophores to the primer. Thus, various commercial primers are available, such as primers from pUC/M13, λgt10, λgt11, and the like. See, Sambrook et al., *Molecular Cloning: A Laboratory Manual*, 2nd ed., CSHL, 1989, Section 13. DNA sequences are cloned in an appropriate vector having a primer sequence joined to the sequence to be sequenced. Different 2', 3' ddNTPs are employed, so that termination occurs at different sites, depending upon the particular ddNTP which is present in the chain extension. By employing the subject primers, each ddNTP will be associated with a particular label. After extension with the Klenow fragment, the resulting fragments may then be separated in a single lane by electrophoresis or in a single capillary by electrophoresis, where one can detect the terminating nucleotide by virtue of the fluorescence of the label.

Kits are provided having combinations of labels, usually at least 2. Each of the labels will have the acceptor-donor pair, usually with comparable backbones, where the labels will be separated along the backbone to give comparable mobility in the separation method to be used. Each of the labels in a group to be used together will absorb at about the same wavelength and emit at different wavelengths. Each of the labels in the group will have about the same effect on mobility in the separation method, as a result of the variation in placement of the different fluorophores along the backbone.

The kits will generally have up to about 6, usually about up to about 4 different labels which are matching, but may have 2 or more sets of matching labels, having 2–6 different labels.

Of particular interest are labels comprising a nucleic acid backbone, where the labels will generally have at least about 10 nucleotides and not more than about 50 nucleotides, usually not more than about 30 nucleotides. The labels may be present on the nucleotides which hybridize to the complementary sequence or may be separated from those nucleotides. The fluorophores will usually be joined to the nucleotide by a convenient linking arm of from about 2 to 20, usually 4 to 16 atoms in the chain. The chain may have a plurality of functionalities, particularly non-oxo-carbonyl, more particularly ester and amide, amino, oxy, and the like. The chain may be aliphatic, alicyclic, aromatic, heterocyclic, or combinations thereof, usually comprising carbon, nitrogen, oxygen, sulfur, or the like in the chain.

The entire nucleic acid sequence may be complementary to the 5' primer sequence or may be complementary only to the 3' portion of the sequence. Usually, there will be at least about 4 nucleotides, more usually at least about 5 nucleotides which are complementary to the sequence to be recognized. The primers are combined with the sequence to be recognized in the appropriate plasmid having the primer sequence at the 3' end of the strand to be copied and dNTPs added with a small amount of the appropriate ddNTP. After extension, the DNA may be isolated and transferred to a gel or capillary for separation.

The kits which are employed will have at least two of the subject labels, which will be matched by having substantially the same absorption for the donor molecule, distinct emission spectra and substantially the same mobility. Generally for single stranded nucleic acids, the separation will be from about 3–20, more usually 3–15, preferably about 3–10 nucleosides between fluorophores.

The following examples are offered by way of illustration and not by way of limitation.

EXPERIMENTAL

Design and synthesis of ET primers. The structures of the ET primers and a representative synthetic reaction are presented in FIG. 1. Oligodeoxynucleotides (18-bases long) with the sequence 5'-GTTTTCCCAGTCACGACG-3' (SEQ ID NO:01) (the M13-40 universal primer) were synthesized with donor-acceptor fluorophore pairs separated by different distances. The 18-mer contains a modified base (T*) introduced by the use of 5'-dimethoxytrityl-5-[N-(trifluoroacetylaminohexyl)-3-acrylimido]-2'-deoxyuridine, 3'-[(2-cyanoethyl)-(N,N-diisopropyl)]-phosphoramidite (Amino-Modifier C6 dT, Glen Research, Sterling, Va.) (Structure 1), which has a protected primary

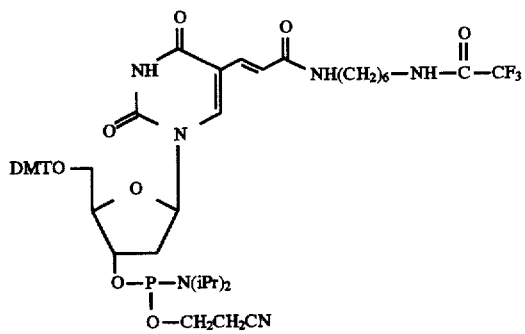

Structure 1. Amino Modifier C6 dT amine linker arm. The donor dye was attached to the 5' end of the oligomer, and the acceptor dye was attached to the primary amine group on the modified base (T*). The ET primers are named using the abbreviation D-N-A, where D is the donor, A is the acceptor, and N is the number of bases between D and A. In all the primers prepared, 5-carboxyfluorescein (FAM, F) is selected as a common donor, 2',7'-dimethoxy-4',5'-dichloro-6-carboxyfluorescein (JOE, J), N,N,N',N'-tetramethyl-6-carboxyrhodamine (TAMRA, T) and 6-carboxy-X-rhodamine (ROX, R) are selected respectively as acceptors. As a representative example, the structure of F3T is shown below (Structure 2).

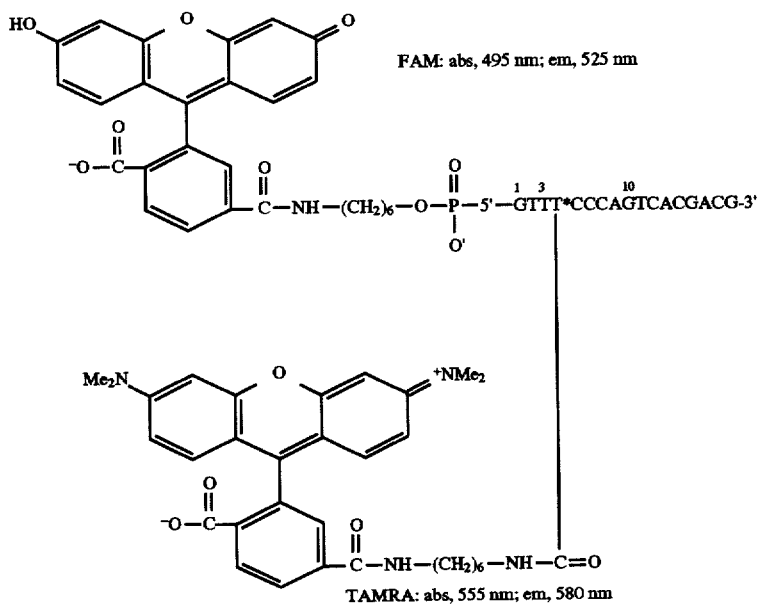

Structure 2. F3T

To prepare the ET primers, the donor FAM was introduced by using 6-FAM amidite in the last step of the oligonucleotide synthesis on a DNA synthesizer. After cleavage from the solid support and removal of the base protecting groups, the primers were evaporated to dryness under vacuum (0.5 mm Hg). To incorporate the acceptor dyes, 15–20 nmol of FAM-labeled T*-containing oligonucleotides in 40 μl 0.5M $Na_2CO_3$/NaHCO (pH 9.0) buffer were incubated overnight at room temperature with an approximately 150-fold excess of corresponding FAM, JOE, TAMRA and ROX N-hydroxysuccinimidyl esters in 12 μl DMSO. Unreacted dye was removed by size exclusion chromatography on a Sephadex G-25 column (Pharmacia, Piscataway, N.J.). The ET primers were then purified by electrophoresis in a 20% polyacrylamide gel containing 6M urea (40 cm×0.8 cm). The purified primers were recovered from the gel slices and desalted with Oligonucleotide Purification Cartridge (Applied Biosystems, Foster city, Calif.). The single dye-labeled primers with the same sequence as that of the ET primers were prepared by the standard protocol using Aminolink 2 (Applied Biosystems, Foster city, Calif.). The purity of the primers was shown to be >99% by polyacrylamide capillary gel electrophoresis. Primers were quantified by their 260 nm absorbances and then stored in 10 mM Tris-Cl, 1 mM EDTA (pH 8.0) at a final concentration of 0.4 pmol/μl for DNA sequencing reactions.

Figure 3:
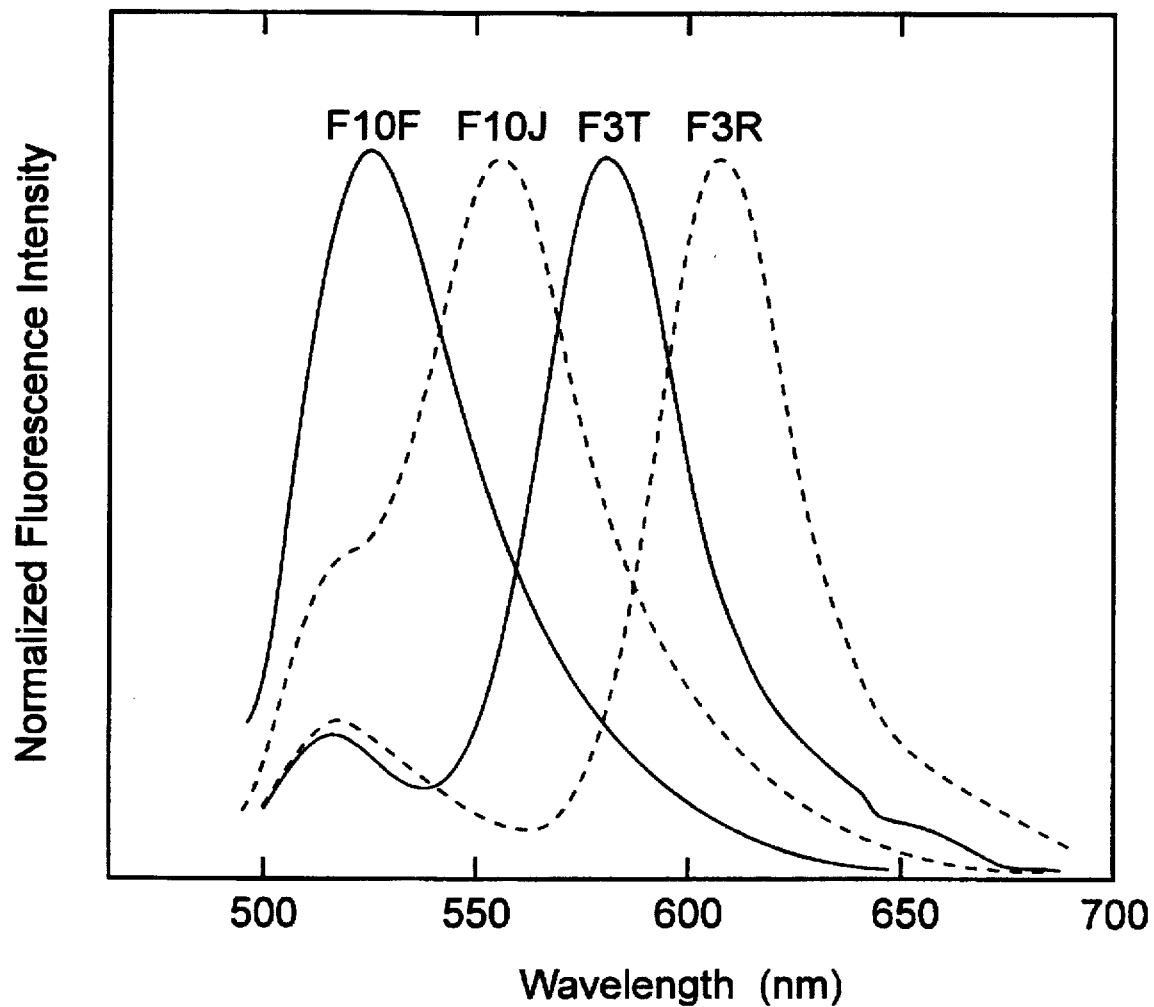
FIG. 3 shows the normalized fluorescence emission spectra of the four ET primers (F10F, F10J, F3T and F3R) (1×TBE, 7M urea).
Figure 4C:
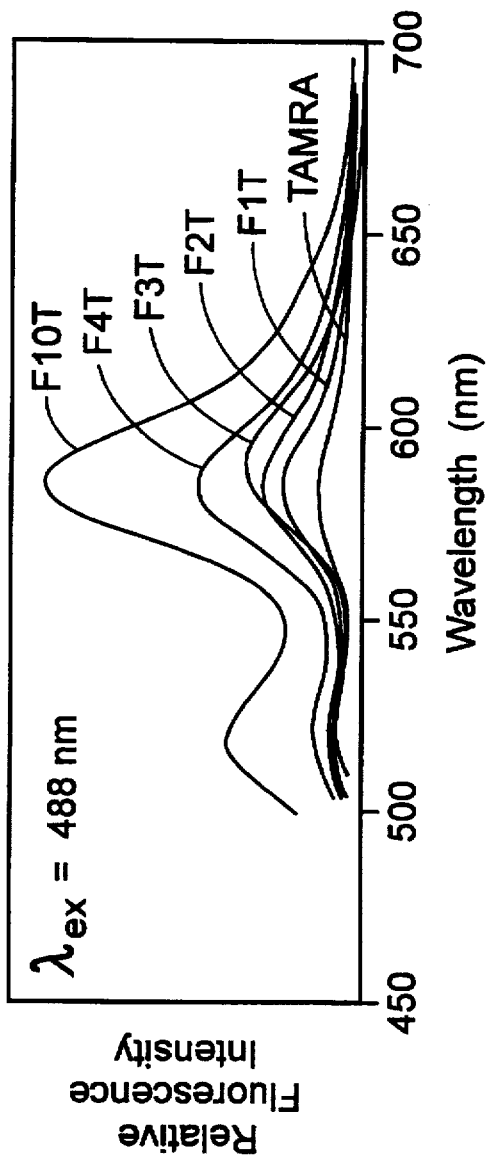
Figure 4D:
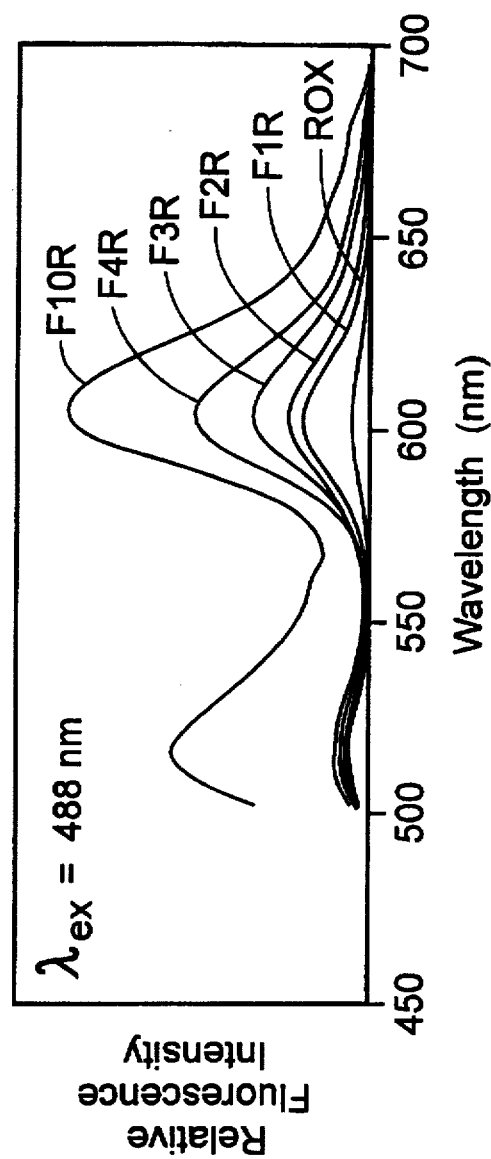
Figure 5:
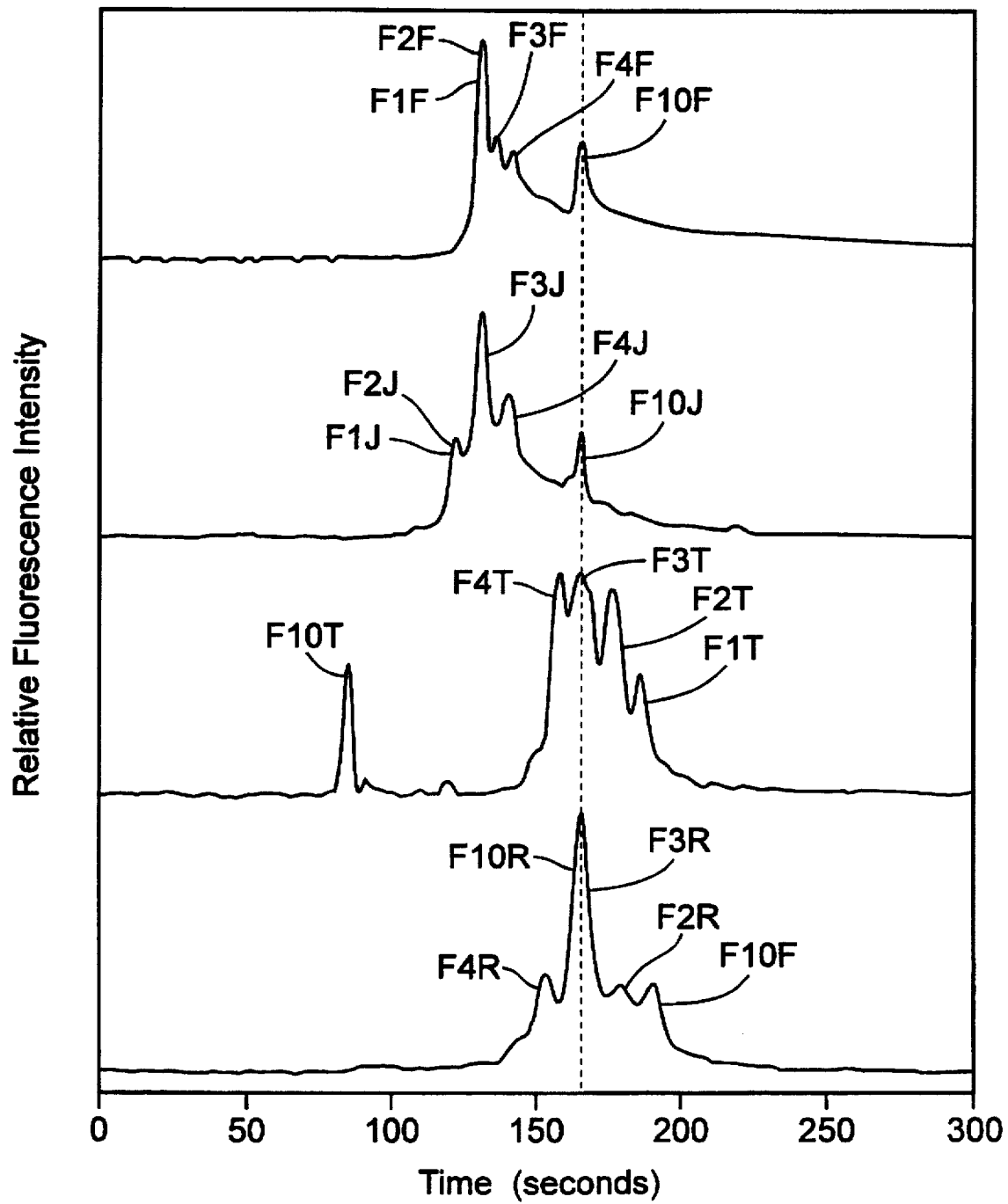
FIG. 5 shows capillary electropherograms of each ET primer series. A separate experiment has established that F10F, F10J, F3T and F3R have very similar mobilities. The mobilities of the other primers are shown for each set, relative to that of F10F, F10J, F3T and F3R, respectively. Sample was analyzed by typical capillary electrophoresis (CE) DNA sequencing conditions with 488 nm excitation.
Figure 6:
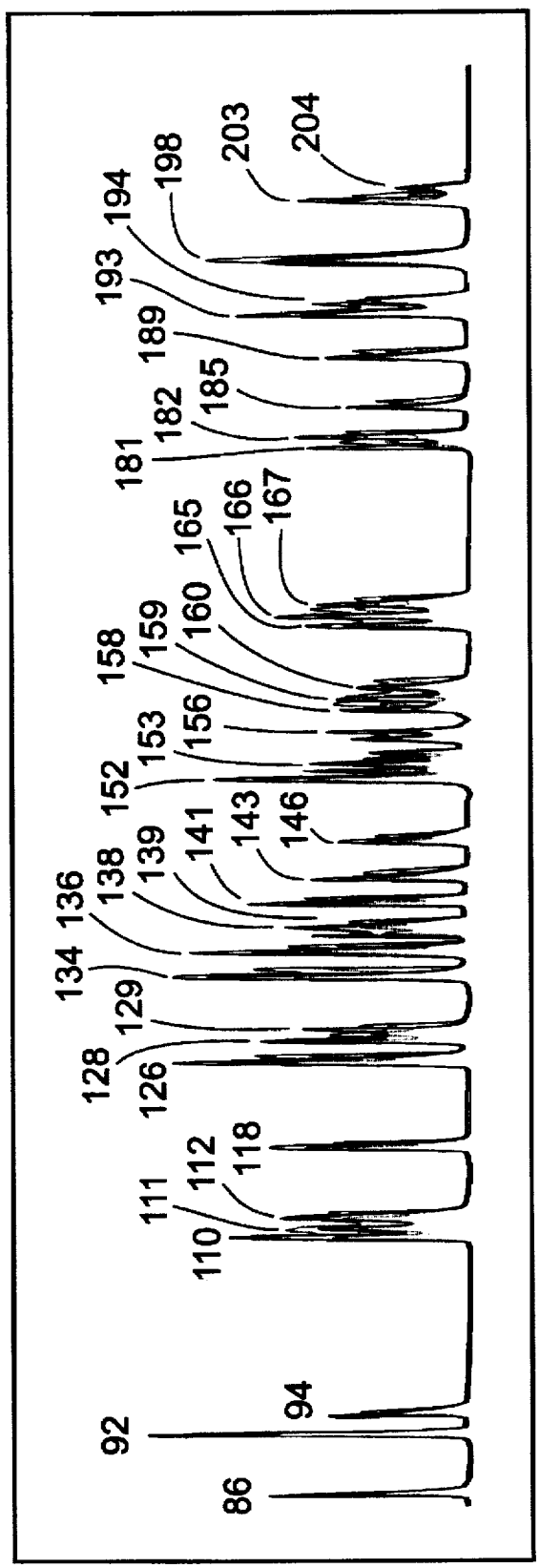
FIG. 6 shows that the mixed single base (ddATP/dNTPs) DNA sequencing fragments generated with F10F, F10J, F10T and F10R individually and then combined together have substantially the same mobility shift. Samples were prepared using Sequenase 2.0 Kit (USB/Amersham LIFE SCIENCE) and run on a 4-color CE DNA sequencer.

Twenty ET primers were synthesized with the same donor at 5' end and different acceptors at different positions on the primer sequence. The spacing between the two chromophores is altered by varying the position of T* in the synthesis of each primer. We found that the electrophoretic mobility of the ET primers depends on the spacing between the donor and acceptor. Within a range of distances determined by the number of intervening bases that allow good energy transfer, it is possible to adjust the electrophoretic mobility of the primers. The advantages of the energy transfer approach described here are (1) that a large Stokes shift and much stronger fluorescence signals can be generated when exciting at 488 nm and (2) that the mobility of the primers can be tuned by varying the distances between the donor and acceptor to achieve the same mobility. As a representative example, FIG. 2A, 2B, 2C, and 2D present the absorption and emission spectra of the ET primer F10F, F10J, F3T and F3R respectively. Each ET primer exhibits the characteristic absorption of FAM at 496 nm as well as strong absorption at 525 nm due to JOE in F10J, at 555 nm due to TAMRA in F3T and at 585 nm due to ROX in F3R. The fluorescence spectra of the ET primers are dominated by the acceptor emissions. While the emission maximum of F10F is at 525 nm, the emission of F10J with 488-nm excitation is Stokes-shifted to 555 nm, that of F3T is shifted to 580 nm, and that of F3R is shifted to 605 nm. In the case of F3R, the Stokes shift is over 100 nm. FIGS. 2A, 2B, 2C, and 2D also presents emission spectra of the single dye-labeled primers measured at the same molar concentration as that of the corresponding ET primers. Substantial enhancement of the ET primer emission intensity is observed compared to the corresponding single dye-labeled primers, indicating that efficient energy transfer is occurring. The fluorescence intensity improvements derived from FIGS. 2A, 2B, 2C, and 2D are: F10F=1.8×FAM; F10J=2.5×JOE or 1.4×JOE when JOE is excited at 514 nm; F3T=5.3×TAMRA or 1.7×TAMRA when TAMRA is excited at 514 nm; F3R= 6.2×ROX or 2.3×ROX when ROX is excited at 514 nm. Thus, the fluorescence intensity of single JOE, TAMRA and ROX labeled primer with 514 nm excitation is still less than that of the corresponding ET primer with 488 nm excitation. To evaluate the emission spectral purity of the four ET primers, their normalized emission spectra are presented in FIG. 3. It can be seen that the residual emission of FAM in F10J, F3T and F3R is very small. Based on a comparison of the residual FAM emission in the ET primers with that of a FAM-labeled primer with same sequence and length, the energy transfer efficiency was calculated to be 65% for F10J, 96% for F3R and 97% for F3T. FIGS. 4A, 4B, 4C, and 4D presents the fluorescence intensity comparison of the ET primer series as well as the corresponding single dye-labeled primers measured at the same molar concentration. The results indicate that when the two fluorophores are too close to each other, fluorescence quenching occurs. The fluorescence intensity increases with the increase of the separation distances between the donor and acceptor. Strong fluorescence signals were obtained when the separation distance is 10-bases. The fluorescence intensity of F10T and F10R measured at the acceptor emission region is 10 and 14 times that of TAMRA and ROX primer respectively. Thus, the maximum fluorescence signals can be increased as much as 14-fold using the ET principle. The results also indicate that the donor FAM emission intensity in F10T and F10R is higher than the other ET primers. However, for a particular primer, as long as the acceptor emission is higher than or equal to that of the donor and the net fluorescence signal is intense, it is valuable for DNA analysis. The mobility comparison of ET primers on polyacrylamide capillary electrophoresis are shown in FIG. 5 which indicates that F10F, F10J, F10R, F3T and F3R have very similar mobility shifts. Although F10T has large mobility difference compared to F10F, F10J and F10R, FIG. 6 shows that the extended ddAPT/dNTPs DNA fragments generated with F10T have similar mobilities as those generated with F10F, F10J and F10R. This indicates that as the DNA fragments grow longer than 18 bases, DNA fragments generated with F10T have essentially the same conformation as fragments generated with F10F, F10J and F10R. For the successful application of donor-acceptor fluorophore labeled primers to DNA sequencing, it is useful that the primers produce same mobility shifts of the DNA fragments and display distinct fluorescence signals. Six primers (F10F, F10J, F10T, F10R, F3T and F3R) were therefore selected for evaluation in DNA sequencing.

DNA Sequencing procedure. Sequencing was performed using M13mp18 template DNA and modified T7 DNA polymerase on a 4-color capillary electrophoresis (CE) DNA sequencer designed in our laboratory and on an ABI 373A sequencer. Four reactions were run, one for each dye/ddNTP combination. The reactions containing ddCTP were run with the F10F primer, ddATP with the F10J primer, ddGTP with the F3T or F10T primer, and ddTTP with the F3R or F10R primer. The working buffer was prepared by freshly mixing equal volumes of 400 mM MOPS (pH 7.5), 500 mM NaCl, 100 mM MgCl$_2$ (10×MOPS buffer) and 50 mM MnCl$_2$, 150 mM sodium isocitrate (10×Mn buffer). One μl of this buffer was then combined with 1μl of primer (0.4 pmol), the indicated amount of template DNA, and water to a total volume of 5 μl. The mixtures were annealed by heating at 65° C. for 2 min and slowly (~35 min) cooling to <30° C. Three μl of dNTP/ddNTP mix (2.4 mM each of dGTP, dATP, dTTP and dCTP with 8 μM of the specific ddNTP) were then added and the reaction mixture warmed to 37° C. for 2 min. Then 2 μl of a freshly diluted mixture of T7 DNA polymerase (2 units/μl) and yeast pyrophosphatase (1.5 units/ml) were added and incubation continued at 37° C. for 30 min. The four reaction mixtures for each sequence were then stopped and combined into one vial and 4 μl of 3M sodium acetate and 180 μl of 95% ethanol were added to precipitate the DNA fragments. After 15 min at −20° C., the precipitated DNA was collected by centrifugation (12,000 ×g) for 15 min, and washed twice with 70% ethanol. The precipitated DNA was vacuum dried, and resuspended in 2 μl 98% formamide containing 1 mM EDTA (for CE sequencer) or 5 μl of deionized formamide containing 8.3 mM EDTA (for ABI sequencer) and heated at 95° C. for 2 min. For CE sequencer, samples were introduced electrophoretically into a 65 cm long (45 cm effective length) 3%T and 3%C polyacrylamide gel filled capillary. Electrophoresis was run at 150 V/cm. One argon laser at 488 nm is used for excitation and the fluorescence signals were collected in four channels centered at 525, 555, 580 and >610 nm. For ABI sequencer, the denatured DNA was loaded on a 6% polyacrylamide 8.3M urea denaturing gel mounted in the instrument. Electrophoresis was conducted at a constant power of 35 W for 12-14 hours using Tris-taurine-EDTA buffer. The data were analyzed using the ABI 373A software (version 1.2.0).

Figure 7:
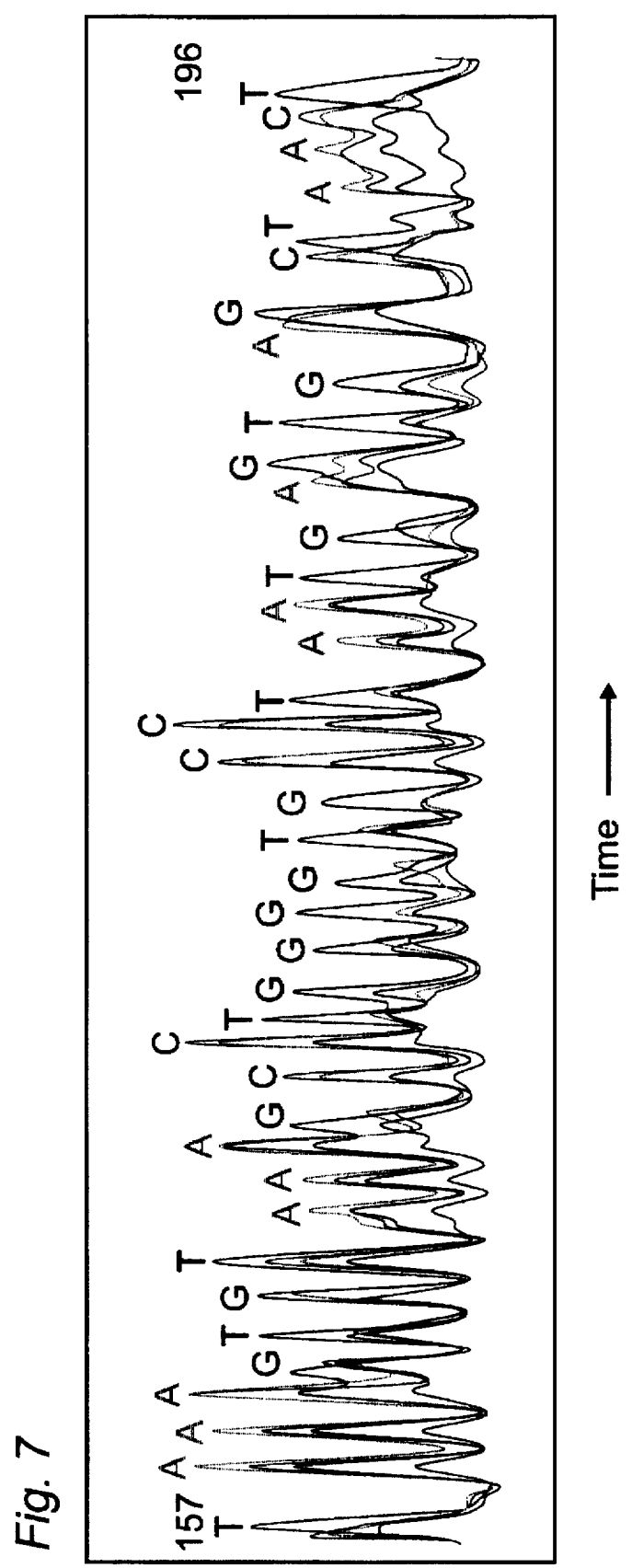
FIG. 7 shows a portion of 4-color raw data (base 157 to 196) of DNA sequencing profile of M13mp 18 DNA using the ET primer F10F, F10J, F10T and F10R and Sequenase 2.0. Primer concentration: 0.4 pmol; DNA template: 0.8 µg (0.2 µg for each base extension).
Figure 8E:
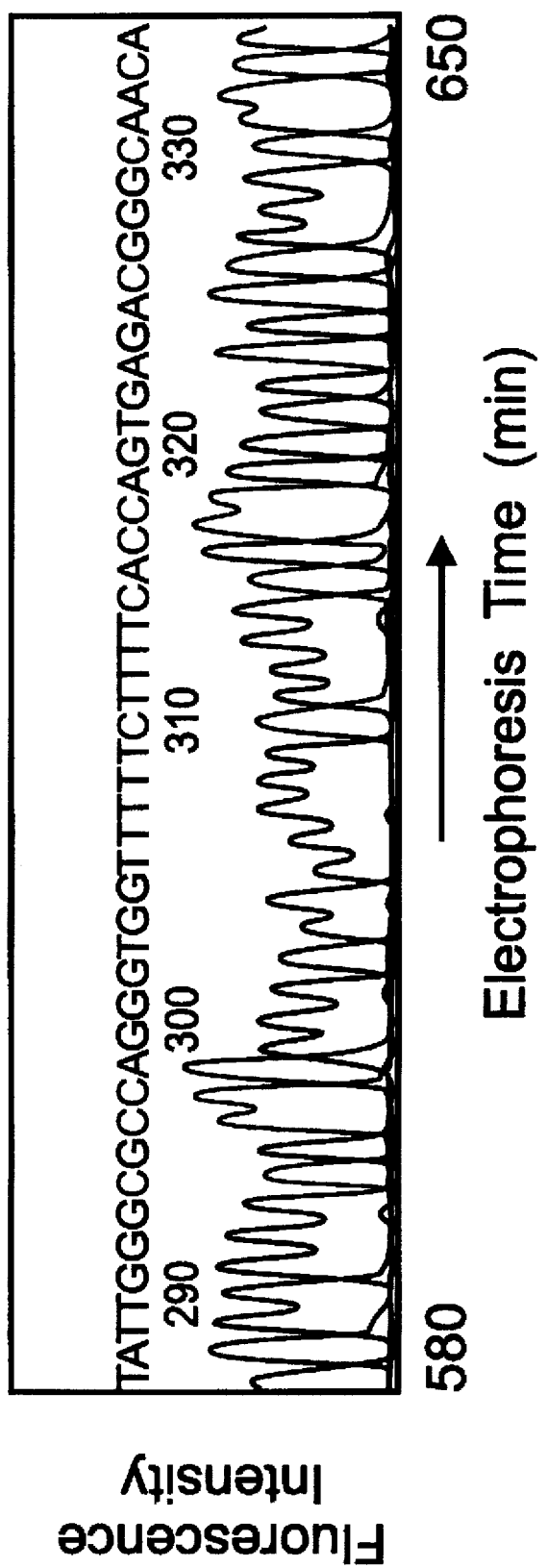

DNA sequencing results with ET primers. DNA sequencing using primer F10F, F10J, F10T and F10R on CE sequencer was performed using 0.4 pmol of primer and 0.2 μg of template DNA for each base extension. The sequences extended to more than 600 bases, a portion of which (raw data) is shown in FIG. 7. From this raw data, sequences can be determined by the color on the top peak of the electropherograms. This is the first 4-color sequencing plot without any mobility shift adjustment.

ET primers described here also provide better results and higher sensitivity on the commercial 4-color DNA sequencer. To demonstrate the advantage of ET primers versus conventional single-dye labeled printers. DNA sequencing samples generated with primer F10F, F3T and F3R were analyzed on an Applied Biosystems 373A sequencer. Single base extension (ddTTP/dNTPs) experiments were performed to examine the relative mobility shift and sensitivity of DNA fragments generated with the ET primers. FIGS. 8A, 8B, 8C, 8D, and 8E present raw fluorescence intensity traces from electrophoresis run on an ABI 373A sequencer. The graphs in FIG. 8A were obtained using M13 (−40) primers labeled with single dye molecules. The differences in electrophoretic mobility of the DNA fragments can be clearly seen. The TAMRA- and ROX-labeled fragments migrate about one base slower than the FAM- and JOE-tagged DNA fragments and have dramatically weaker fluorescence intensities. The corresponding runs with the ET primers are presented in FIG. 8B. The mobilities of the DNA fragments are more closely matched (less than a quarter of a base difference).

To further quantify the instrument sensitivity with the ET primers under slab gel conditions, reactions were run using a constant amount of primer (0.4 pmol) and varying the amount of M13mp18 template DNA (0.05–1 pmol). Graphs of several band intensities against quantity of template were made. This method indicates that the sensitivity for the F10F primer is 160% that of the FAM primer. Similarly, the sensitivity for the F10J, F3T and F3R primers is 360%, 400% and 470% that of JOE, TAMRA and ROX primers, respectively. In experiments which included an excess of template DNA over primer, only a small fraction of either ET or single-dye labeled primer remained unextended. Thus, no significant difference was seen in the efficiency with which the ET primers were extended by polymerase compared with single-dye labeled primers.

Typical raw fluorescence intensity traces for 4-dye, single lane sequences are presented in FIGS. 8C and 8D. Shown here is a portion from the middle of the run spanning about 45 bases. On this intensity scale, the peaks from the red filter are barely discernible when single ROX-labeled primer is used (c). In contrast, all of the sequence-dependent intensity fluctuations are readily seen with the ET primers in the raw data (D). While four-color sequences run with this instrument typically require 3-fold more template and 2-fold more primer in the reactions containing TAMRA- and ROX-labeled primers, the four reactions used for FIG. 8D contained equal amounts of ET primer and template. This change in reaction balance was made possible by the increased relative intensities of the F3T and F3R primers. With these four primers, DNA sequencing on M13Mp18 template produces 510 bases with accuracy of over 99.8%. This sequence can be obtained using a total of 0.6 μg (0.24 pmol) of M13 template DNA which is approximately one-fourth the amount of template DNA required to give similar sequence accuracy with single dye-labeled primers.

It is evident from the above results, that one can tune related compositions, e.g. polynucleotides functionalized with 2 fluorophores to provide for different emission wavelengths and high emission quantum yields, while having substantially the same excitation-light absorbance and mobility. In this way, mixtures of compositions may be independently analyzed, where the different components may be differentially labeled with labels having differing fluorescence emission bands. Furthermore, the compositions can be readily prepared, can be used in a wide variety of contexts, and have good stability and enhanced fluorescent properties.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identification and detection of components in a multicomponent mixture employing different fluorescent labels to detect at least two components of interest, wherein said labels are characterized by: (1) having a donor-acceptor fluorescent pair bonded to an oligonucleotide chain with energy transfer from said donor to said acceptor; and (2) each of the labels absorbs at substantially the same wavelength and emits at a different wavelength;

said method comprising:

binding different labels to different components of said multi-component mixture;

detecting each of said labeled components by irradiating at the absorption wavelength of said donor and detecting the fluorescence of each of said labels.

2. A method according to claim 1, wherein said donor absorbs light in the wavelength range of 350–800 nm and said acceptor emits light in the wavelength range of 450–1000 nm.

3. A method according to claim 2, wherein said acceptor-donor pair are 9-phenylxanthenes.

4. A method of separating components of a multicomponent mixture, wherein each of the different components of interest are labeled with different labels, wherein said labels are characterized by: (1) having a donor-acceptor fluorescent pair bonded to an oligonucleotide chain with efficient energy transfer from said donor to said acceptor; (2) each of the labels absorbs at substantially the same wavelength and emits at a different wavelength; (3) and each of the different labels has substantially the same mobility in said separation as a result of varying the spacing of said donor-acceptor pair along said oligonucleotide chain;

said method comprising:

binding different labels to different components of said multi-component mixture;

separating said multi-component mixture into individual fractions; and detecting each of said labeled components by irradiating at an absorption wavelength of said donor and detecting the fluorescence of each of said labels.

5. A method according to claim 4, wherein said separation is by electrophoresis.

6. A method according to claim 4, wherein said donor absorbs light in the wavelength range of 350–800 nm and said acceptor emits light in the wavelength range of 450–1000 nm.

7. A method according to claim 6, wherein said acceptor-donor pair are 9-phenylxanthenes.

8. In a method for sequencing a nucleic acid which employs primers for copying a single stranded nucleic acid and dideoxynucleotides for terminating the chain at a particular nucleotide resulting from said copying, said method comprising:

cloning a nucleic acid fragment to be sequenced into a vector comprising a primer binding sequence 5' to said fragment complementary to a primer, or ligating an oligonucleotide primer binding sequence to a DNA fragment to be sequenced, where the sequence of said oligonucleotide is complementary to a primer;

copying said fragment with a DNA polymerase in the presence of said primer, dNTPs and each of a plurality of dideoxynucleotides in separate reaction vessels, to generate single stranded DNA sequencing fragments; and separating the resulting mixture of single stranded DNA sequencing fragments and determining the sequence by means of the bands present on the gel;

the improvement which comprises:

employing primers which are characterized by:

(1) having an acceptor-donor fluorescent pair bonded to a nucleic acid chain complementary to said primer binding sequence, where the donor transfers energy to said acceptor for enhanced fluorescence of said acceptor; (2) each of the primers absorbs at substantially the same wavelength and emits at a different wavelength; and (3) each of the primers has substantially the same mobility in said separation, resulting from varying the spacing and fluorophores of said donor-acceptor pair along said nucleic acid chain.

9. A method according to claim 8, wherein one of the members of said acceptor-donor fluorescent pair is bonded to the 5' terminus of said primer.

10. A method according to claim 8, wherein there are four primers having different acceptor-donor pairs.

11. A method according to claim 8, wherein said acceptor-donor fluorescent pair is separated by not more than 20 nucleotides.

12. A method according to claim 8, wherein at least two acceptor-donor fluorescent pairs are xanthene compounds.

13. A method according to claim 12, wherein said xanthene compounds comprise fluorescein derivatives and rhodamine derivatives.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear

```
( i i ) MOLECULE TYPE: other nucleic acid
    ( A ) DESCRIPTION: /desc ="Synthesized Primer"

( x i ) SEQUENCE DESCRIPTION: SEQ ID NO:1:

GTTTTCCCAG TCACGACG                                                        1 8
```